(12) United States Patent
Mizutani et al.

(10) Patent No.: US 6,569,140 B1
(45) Date of Patent: May 27, 2003

(54) ABSORBENT ARTICLE

(75) Inventors: Satoshi Mizutani, Kagawa (JP); Tatsuya Tamura, Kagawa (JP); Yuuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/707,391

(22) Filed: Nov. 7, 2000

(30) Foreign Application Priority Data

Nov. 19, 1999 (JP) .......................................... 11-329283

(51) Int. Cl.[7] .............................................. A61F 13/15
(52) U.S. Cl. ............................ 604/385.28; 604/385.04; 604/385.24
(58) Field of Search ....................... 604/385.28, 385.01, 604/385.24, 385.25, 385.26, 385.27, 385.54

(56) References Cited

U.S. PATENT DOCUMENTS

| 4,025,996 | A | * | 5/1977 | Saveker ........................ 428/594 |
| 5,582,606 | A | * | 12/1996 | Bruemmer et al. ..... 604/385.28 |
| 5,601,546 | A | * | 2/1997 | Tanji et al. .............. 604/385.2 |
| 5,624,424 | A | * | 4/1997 | Saisaka et al. ............ 604/385.2 |
| 5,624,426 | A | * | 4/1997 | Roe et al. ................. 604/385.2 |
| 5,643,244 | A | * | 7/1997 | Yamaki et al. ............ 604/385.2 |
| 5,681,303 | A | * | 10/1997 | Mills et al. ............. 604/385.26 |
| 6,045,545 | A | * | 4/2000 | Vandemoortele et al. ... 604/382 |
| 6,102,892 | A | * | 8/2000 | Putzer et al. .......... 604/385.01 |
| 6,383,431 | B1 | * | 5/2002 | Dobrin et al. .............. 264/154 |

FOREIGN PATENT DOCUMENTS

| JP | 8-21524 | 1/1996 |
| JP | 9-503934 | 4/1997 |
| WO | 95/08972 | 4/1995 |

* cited by examiner

*Primary Examiner*—Weilun Lo
*Assistant Examiner*—Jacqueline Stephens
(74) *Attorney, Agent, or Firm*—Darby & Darby

(57) ABSTRACT

There is disclosed an absorbent article including: a body portion including, a liquid permeable front surface sheet for facing the wearer, a back surface sheet, and an absorbent layer sandwiched between the front surface sheet and the back surface sheet; and leakage preventing walls extending in a longitudinal direction of the body portion and arranged at two sides thereof in a width direction perpendicular to the longitudinal direction. The leakage preventing wall includes a side wall part upstanding from the surface of the body portion and a skin contacting part extending from the upper end of the side wall part toward the outside of the body portion in the width direction. A fold inducing part is formed to extend in the longitudinal direction at a middle part between the upper end and the lower end of the side wall part, whereby the side wall part is folded with the fold inducing part moved toward the outside of the body portion in the width direction when the skin contacting part is pressed toward the surface of the body portion.

7 Claims, 6 Drawing Sheets

ABSORBENT ARTICLE

BACKGROUND OF THE INVENTION

1. Field of the Invention

The present invention relates to an absorbent article including a sanitary napkin and a disposable diaper, and more particularly, it relates to an absorbent article having leakage preventing walls at two sides thereof.

2. Description of the Related Art

Absorbent articles, such as a sanitary napkin and a disposable diaper, sometimes have leakage preventing walls which extend in the longitudinal direction and are arranged in the width direction at two sides on the surface thereof.

For example, Japanese Unexamined Patent Publication (Kokai) No. Heisei 8-21524 discloses an absorbent article having leakage preventing walls which are prepared from webs deformed into a non-planar shape by machine work. The leakage preventing wall formed from the web functions as an elastic strip exhibiting an elastic contractive force in the longitudinal direction of the absorbent article.

In International Unexamined Patent Publication (Kohyou) No. Heisei 9-503934, on the other hand, there is disclosed an absorbent article formed with elastic pleats at two sides in the width direction thereof. The elastic pleat portion has a surface to face the skin so that the elastic pleats are in contact with the skin upon wearing. The elastic pleat portion entirely has a Z-shaped cross section.

As described in the foregoing, the conventional absorbent articles have a leakage preventing wall formed from a web deformed into a non-planar shape or formed with elastic pleats.

However, the conventional leakage preventing wall itself functions as an elastic body for upstanding from the surface of the absorbent article or for incurvating the absorbent article. Therefore, it has such a defect that a body fluid is liable to be retained in a concave part of an irregular shape (i.e., the non-planar shape or the pleat shape), and contamination due to the body fluid is liable to remain on the leakage preventing wall itself.

In the absorbent article disclosed in Japanese Unexamined Patent Publication (Kokai) No. Heisei 8-21524, moreover, since the leakage preventing wall formed from the non-planar web upstands perpendicularly on the surface, the leakage preventing wall is liable to fall down when the leakage preventing wall is in contact with the skin of the wearer. If the leakage preventing wall falls down toward the center of the surface at this time, a part of the absorption region on the surface is covered with the leakage preventing wall to reduce the substantial liquid absorbent area, whereby the entire liquid absorbing performance is lowered.

In the absorbent article disclosed in International Unexamined Patent Publication (Kohyou) No. Heisei 9-503934, on the other hand, since the elastic pleats are arranged in substantially parallel to the surface of the absorbent article, it has such a problem that a body fluid attached to the concave part of the elastic pleat portion is difficult to flow down toward the surface of the absorbent article, whereby the body fluid is liable to remain in the concave part.

Furthermore, because both the leakage preventing walls are formed to have an elastic force by themselves, the leakage preventing walls per se have a low rigidity. Accordingly, when they are provided to upstand from the surface of the absorbent article, for example, the buckling strength of the leakage preventing wall cannot be so high. Therefore, when a leakage preventing wall having a steric shape is formed, it is difficult to maintain the steric shape.

SUMMARY OF THE INVENTION

An object of the invention is to provide an absorbent article having a leakage preventing wall which is difficult to fall down on a liquid absorption region on contacting with the skin of the wearer, so as not to decrease the absorbent area on the surface of the absorbent article.

Another object of the invention is to provide an absorbent article having a leakage preventing wall which prevents a body fluid attached thereto from being retained in a concave part of an irregular shape of the leakage preventing wall.

A further object of the invention is to provide an absorbent article having a leakage preventing wall of a high rigidity and a high buckling strength, which is difficult to fall down due to a pressure caused by contact with the skin, whereby the steric shape of the leakage preventing wall can be maintained.

According to one aspect of the invention, there is provided an absorbent article comprising:

a body portion including a liquid permeable front surface sheet for facing the wearer, a back surface sheet, and an absorbent layer sandwiched between the front surface sheet and the back surface sheet; and leakage preventing walls extending in a longitudinal direction of the body portion and arranged at two sides thereof in a width direction perpendicular to the longitudinal direction, the leakage preventing wall including a side wall part upstanding from the surface of the body portion and a skin contacting part extending from the upper end of the side wall part toward the outside of the body portion in the width direction, a fold inducing part being formed to extend in the longitudinal direction at a middle part between the upper end and the lower end of the side wall part, whereby the side wall part is folded with the fold inducing part moved toward the outside of the body portion in the width direction when the skin contacting part is pressed toward the surface of the body portion.

Preferably, both ends in the longitudinal direction of the leakage preventing wall are fixed on the surface of the body portion in such a state that the side wall part is folded with the fold inducing part moved toward the outside of the body portion in the width direction and the skin contacting part is superposed on the folded side wall part.

With the fold inducing part being provided, the leakage preventing walls are folded compactly at two sides on the surface of the body portion when the skin contacting part is brought into contact with the skin of the wearer and pressed toward the surface of the body portion, whereby the leakage preventing wall is difficult to fall down toward the center on the surface. As a result, the liquid absorbent area on the surface of the body portion is not substantially decreased. Furthermore, when both the ends in the longitudinal direction of the leakage preventing wall are fixed in such a folded state on the surface of the body portion, the absorbent article is incurvated in the longitudinal direction, and thus the leakage preventing wall can easily upstand in the middle position between two end edges of the absorbent article.

For easy upstanding of the leakage preventing wall, preferably, elastic members exhibiting a contractive force in the longitudinal direction are attached to the fold inducing part and the skin contacting part.

Preferably, the leakage preventing wall comprises nonwoven fabric formed to have a wavy form, of which top parts and bottom parts are alternately arranged in the longitudinal direction and extend perpendicular to the longitudinal direction.

When the leakage preventing wall is formed with the nonwoven fabric thus shaped, the buckling strength of the side wall part is increased, and the leakage preventing wall is difficult to fall down by a pressure from the skin toward the surface.

Preferably, the fold inducing part has a density that is different from a density of other parts of the side wall part. Also preferably, at least one of side edges of the skin contacting part has a density that is different from a density of other parts of the leakage preventing wall.

When the density of the fold inducing part is differentiated from the density of the other parts, the leakage preventing wall is easily folded at the fold inducing part. When the density of the side edges of the skin contacting part is differentiated, the skin contacting part is easily folded in such a direction that the skin contacting part fits the skin, and the nonwoven fabric is easily folded into two at the side edge on the free end of the skin contacting part.

According to another aspect of the invention, there is provided an absorbent article comprising:

a body portion including a liquid permeable front surface sheet for facing the wearer, a back surface sheet, and an absorbent layer sandwiched between the front surface sheet and the back surface sheet; and leakage preventing walls extending in a longitudinal direction of the body portion and arranged at two sides thereof in a width direction perpendicular to the longitudinal direction, the leakage preventing wall comprising nonwoven fabric formed to have a wavy form, of which top parts and bottom parts are alternately arranged in the longitudinal direction and have a higher density than that of midway parts between the top parts and the bottom parts, and the leakage preventing wall having a slant part slanting to leave from the surface of the body portion toward the outside of the body portion in the width direction.

Preferably, the top parts and the bottom parts of the wavy form have a density of 0.1 g/cm$^3$ or more. The upper limit of the density at the top parts and the bottom parts is preferably about 1.0 g/cm$^3$.

When the density of the top parts and the bottom parts of the wavy form of the nonwoven fabric forming the leakage preventing wall is made higher as above, the buckling strength of the leakage preventing wall can be increased. Moreover, a body fluid attached to the leakage preventing wall can easily flow down the slant part thereof toward the surface of the body portion along the parts having the higher density.

Preferably, the leakage preventing wall has such a structure that the nonwoven fabric is folded into two at a free end of the leakage preventing wall to form an inner gap between two folded portions of the nonwoven fabric.

With the gap being provided, the liquid permeability of the leakage preventing wall can be decreased to improve the leakage preventing effect, and the feeling on contacting with the skin can be softened to improve the wear feeling.

Preferably, an elastic member exhibiting a contractive force in the longitudinal direction is interposed between the two folded portions of the nonwoven fabric, and the elastic member is fixed to the two folded portions of the nonwoven fabric, respectively, at the bottom parts of the wavy form thereof.

Owing to the structure, the leakage preventing wall can have a sufficient contractive force in the longitudinal direction without imparting an excessive elastic contractive force to the elastic member.

PREFERRED EMBODIMENTS OF THE INVENTION

Figure 1:
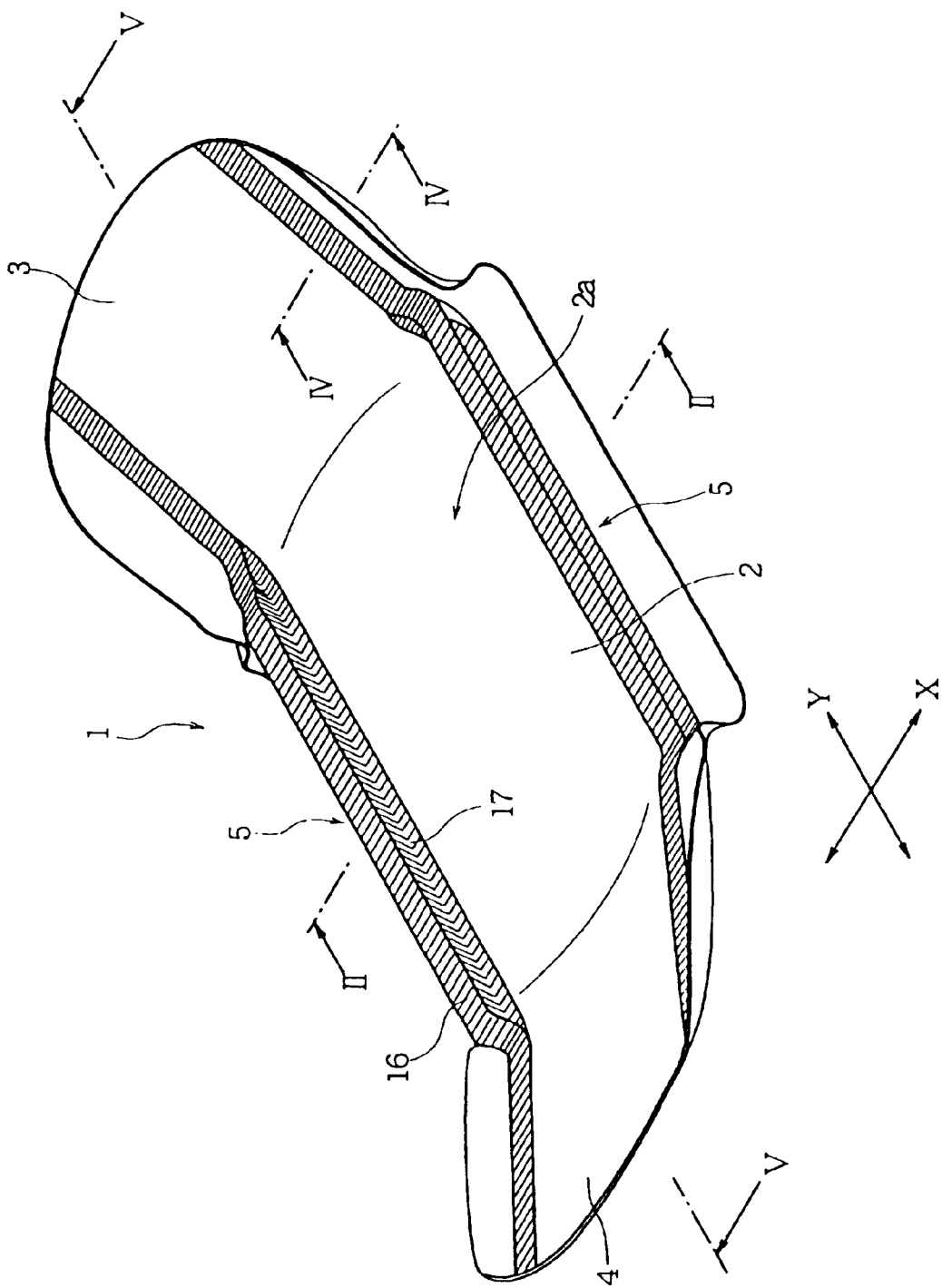
FIG. 1 is a perspective view showing an absorbent article according to one embodiment of the invention.
Figure 2:
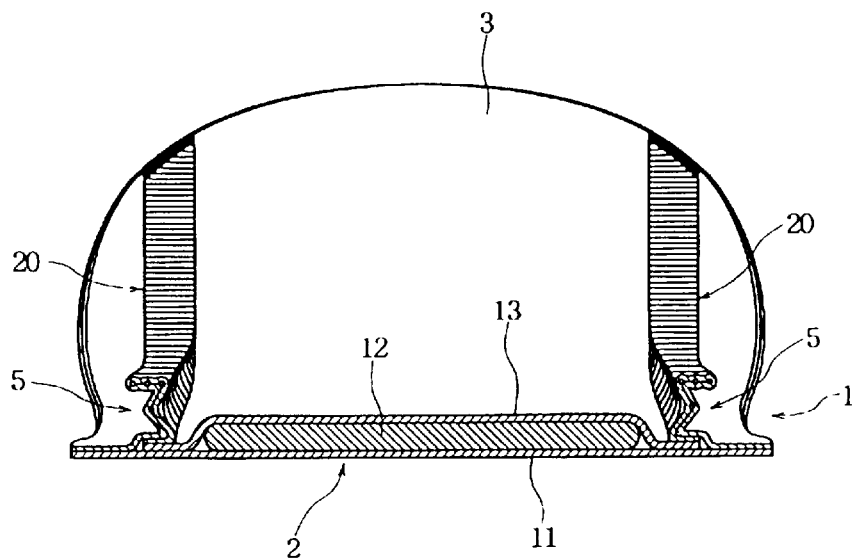
FIG. 2 is a cross sectional view of FIG. 1 taken along line II—II.
Figure 3:
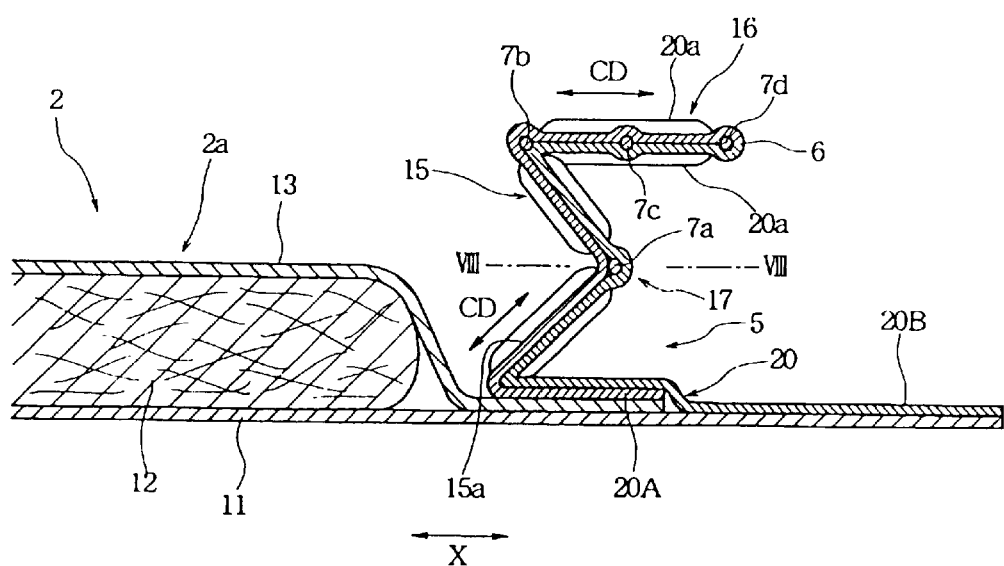
FIG. 3 is a partially enlarged view of FIG. 2.
Figure 4:
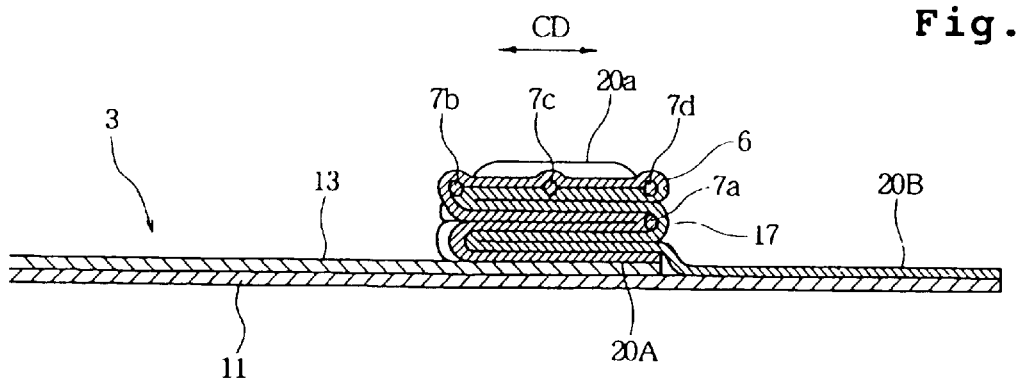
FIG. 4 is a partially enlarged cross sectional view of FIG. 1 taken along line IV—IV.
Figure 5:
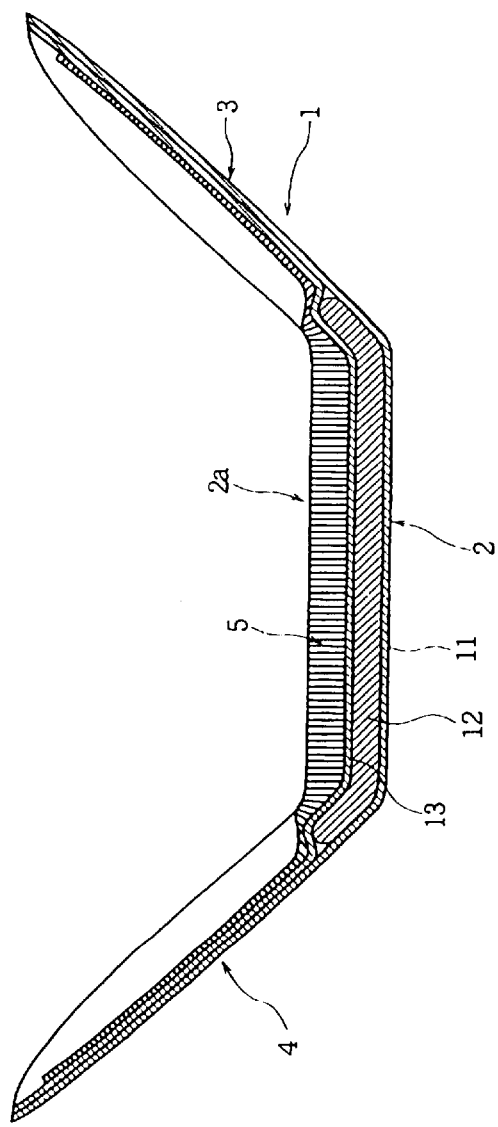
FIG. 5 is a cross sectional view of FIG. 1 taken along line V—V.

FIG. 1 is a perspective view showing a sanitary napkin as an embodiment of the absorbent article of the invention, FIG. 2 is a cross sectional view of FIG. 1 taken along line II—II, FIG. 3 is a partially enlarged view of FIG. 2, FIG. 4 is a partially enlarged cross sectional view of FIG. 1 taken along line IV—IV, and FIG. 5 is a cross sectional view of FIG. 1 taken along line V—V.

In an absorbent article 1 shown in the figures, the direction X is the width direction and the direction Y is the longitudinal direction. An intermediate part 2 is positioned in the middle position between two end edges, and a front part 3 and a back part 4 sandwich the intermediate part 2. Leakage preventing walls 5, 5 extending in the longitudinal direction (Y direction) are provided at two sides (i.e., along two side edges) of the absorbent article 1. The leakage preventing walls 5, 5 can exhibit an elastic contractive force. Owing to the elastic contractive force, the absorbent article 1 is incurvated in the longitudinal direction (Y direction). Mainly in the intermediate part 2, the leakage preventing walls 5, 5 at the two sides upstand from a surface 2a in a steric shape.

As shown in FIG. 5, the absorbent article 1 is constructed to have a body portion including a liquid impermeable back surface sheet 11, an absorbent core 12 superposed thereon, and a liquid permeable front surface sheet 13 further superposed thereon. The absorbent core 12 is provided over the intermediate part 2 and parts of the front part 3 and the back part 4 of the absorbent article 1. The back surface sheet 11 and the front surface sheet 13 are adhered with a hot-melt adhesive or fused by heat embossing in an outer periphery outside the absorbent core 12.

The absorbent core 12 may be made of any suitable material. For example, the absorbent core 12 may be a mixture of crushed pulp and super-absorbent polymer (SAP) wrapped with liquid permeable paper, air-laid pulp sheeted by a binder treatment, absorbent paper, or nonwoven fabric mainly containing hydrophilic fibers. The back surface sheet 11 is liquid impermeable and may be a moisture permeable resin film, nonwoven fabric, or a laminated sheet of the resin film and nonwoven fabric, for example. The front surface sheet 13 is liquid permeable and may be nonwoven fabric made from hydrophilic fibers, porous nonwoven fabric, a porous plastic film, or a laminated sheet of the porous plastic film and nonwoven fabric, for example.

The leakage preventing wall 5 may be made from nonwoven fabric, such as air-through nonwoven fabric, point-bonded nonwoven fabric, spun-bonded nonwoven fabric, spun-lace nonwoven fabric, melt-blown nonwoven fabric and air-laid nonwoven fabric, or a laminated sheet of a plastic sheet, such as of ethylene or polypropylene, and nonwoven fabric. These materials are preferably hydrophobic or water-repellent. The fibers constituting the nonwoven fabric may be polyethylene (PE) fibers, polyethylene terephthalate (PET) fibers or composite fibers of PE/PP or PE/PET, e.g., core-sheath fibers or side-by-side fibers, which have been subjected to a water-repellent treatment.

Figure 7:
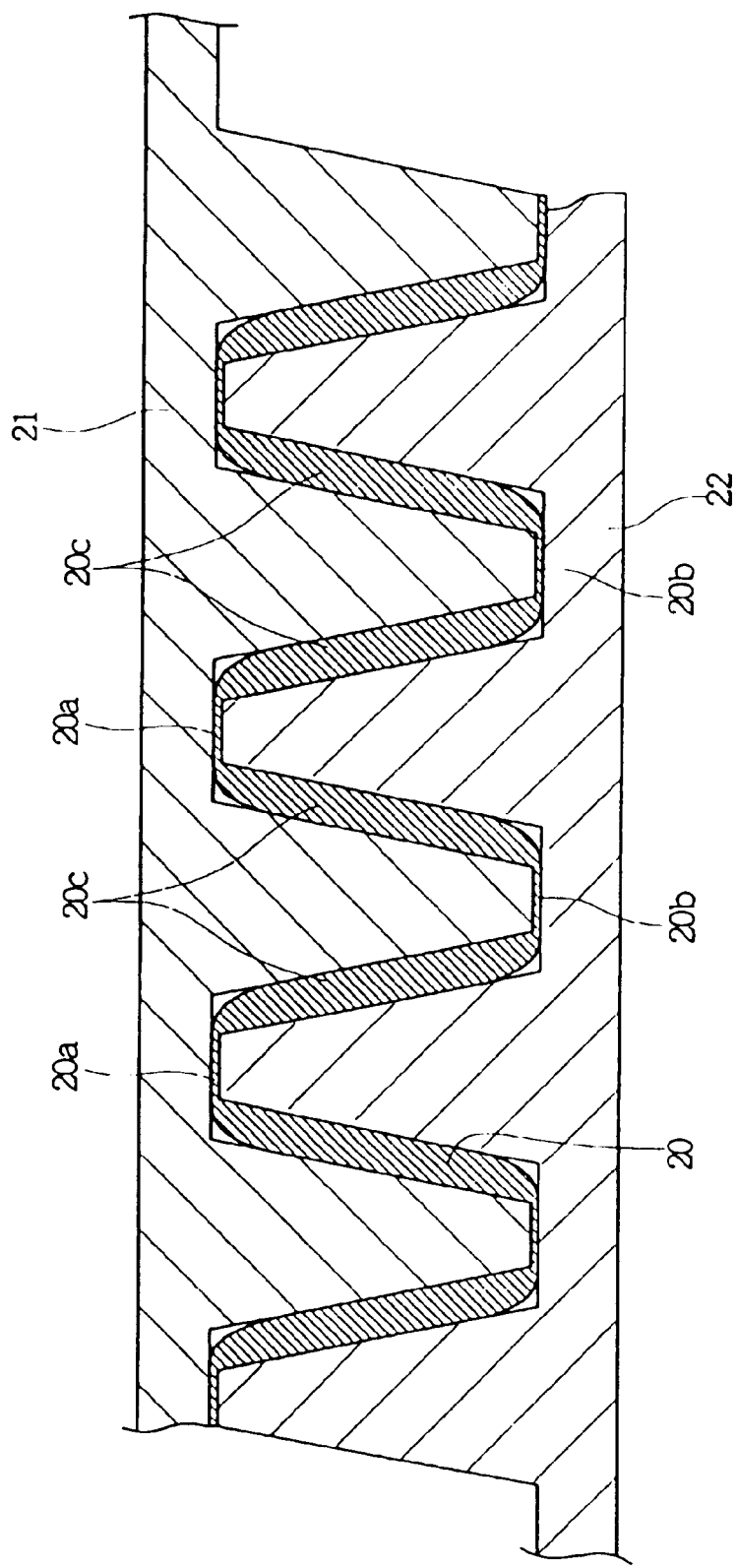
FIG. 7 is a cross sectional view showing an example of a method for forming a sheet constituting a leakage preventing wall.

The sheet forming the leakage preventing wall 5 is heat-pressed to have a wavy form, as shown in FIG. 1. FIG. 7 is a figure for explaining the heat-pressing step, FIG. 8A is an enlarged perspective view of a part of a heat-pressed sheet of FIG. 3, taken from a different angle and sectioned along line VIII—VIII, and FIG. 8B is an enlarged cross sectional view of a part of a heat-pressed sheet of FIG. 3 taken along line extending in CD at a top part of a wavy form.

As shown in FIG. 7, a sheet 20 for forming the leakage preventing wall 5 is heat-pressed between rolls having linearly embossed molds 21 and 22 on the surfaces thereof. For example, the sheet 20 is spun-bonded nonwoven fabric formed from PE/PP core-sheath fibers of a fineness of from 1.1 to 4.4 dtex to have a basis weight of from 15 to 40 g/m². The sheet 20 is subjected to heat-press with the linearly embossed molds 21 and 22 shown in FIG. 7, and the temperature of the molds at this time is preferably from 80 to 120° C. In alternative, the sheet 20 may be preliminary heated to the foregoing temperature range and then pressed by the linearly embossed molds 21 and 22. The pressure of the molds 21 and 22 is preferably within a range from 10 to 30 N (newton).

When the sheet 20 is pressed by the linearly embossed molds 21 and 22, the fibers constituting the sheet 20 are strongly compressed at the top part 20a and the bottom part 20b, while being lightly compressed at the midway part 20c. The sheet 20 having been passed through the linearly embossed molds 21 and 22 has a wavy form, in which the top parts 20a, the bottom parts 20b and the midway parts 20c are repeatedly continued in the Machine Direction (MD) as shown in FIG. 8A. The density of the top part 20a and the bottom part 20b is higher than the density of the midway part 20c. The density at the top part 20a and the bottom part 20b is preferably 0.1 g/cm³ or more. A preferred upper limit of the density at the top part 20a and the bottom part 20b is 1.0 g/cm³.

Figure 8A:
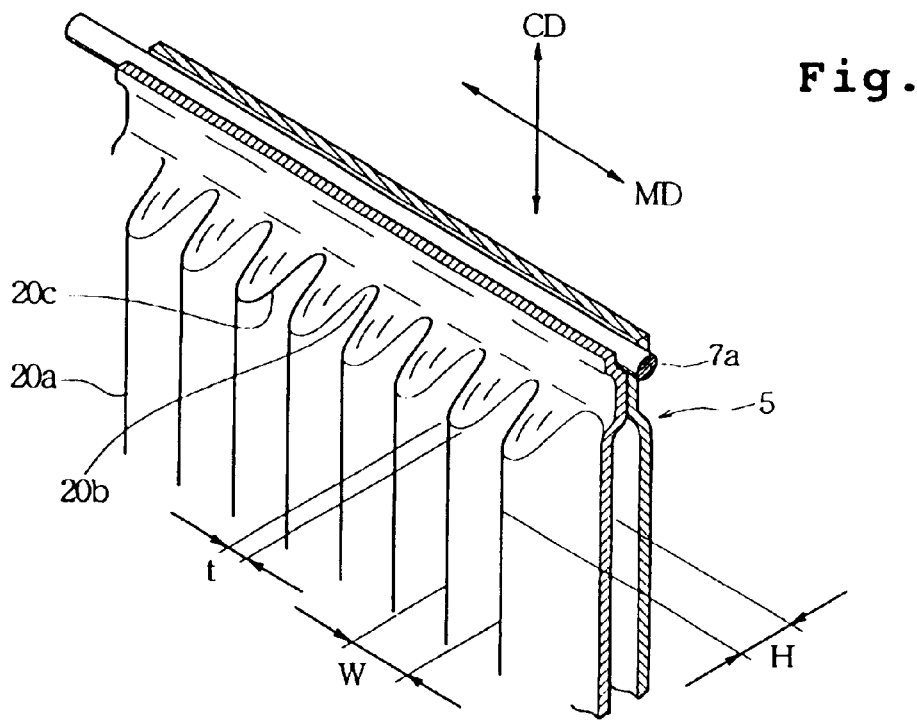
FIG. 8A is an enlarged perspective view of a part of a leakage preventing wall of FIG. 3, taken from a different angle and sectioned along line VIII—VIII.
Figure 8B:
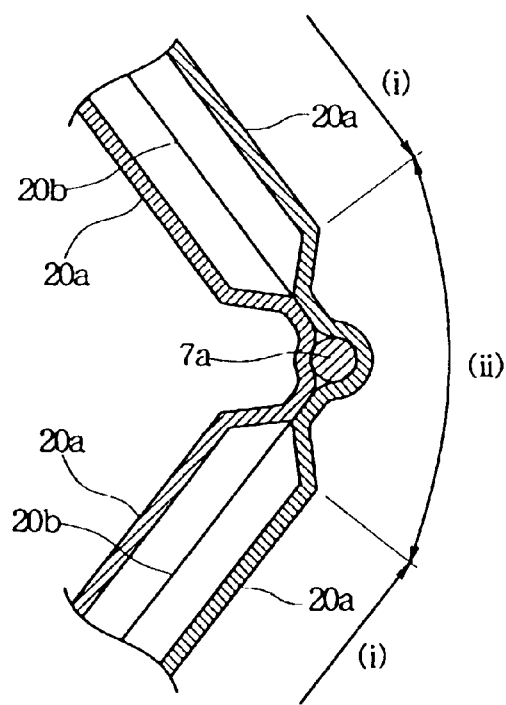
FIG. 8B is an enlarged cross sectional view of a part of a leakage preventing wall of FIG. 3 taken along line extending in CD at a top part of a wavy form.

Since the sheet 20 has the wavy form as shown in FIG. 8A, it is stretchy in the Machine Direction (MD) along which the waves are arranged, and is highly self-supported and has a high buckling strength in the Cross Direction (CD) along which the top parts 20a and the bottom parts 20b extend.

In the sheet 20 formed into the wavy form, it is preferred that the distance W between the central point of the top part 20a and the central point of the top part 20a adjacent to each other is from 0.5 to 3.0 mm, and the width dimension t of the region at the top part 20a and the bottom part 20b having a higher density than the midway part 20c is from 0.1 to 1.0 mm. It is also preferred that the height dimension H between the front surface of the sheet at the top part 20a and the back surface of the sheet at the bottom part 20b is from 0.1 to 0.2 mm.

The elongation ratio of the sheet 20 when it is stretched in the MD along which the waves are arranged is preferably from 1.2 to 2.0 times. The breaking strength in the MD of the sheet 20 is preferably from 18 to 45 N per 1 inch width.

For the leakage preventing wall 5, the sheet 20 formed into the wavy form is used while being folded into two at a free end 6 (see FIG. 3). Elastic members 7a, 7b, 7c and 7d are sandwiched with the sheet folded into two. The elastic members 7a, 7b, 7c and 7d are adhered between two folded portions of the sheet 20 facing to each other, for example, with a hot-melt adhesive.

The elastic members 7a, 7b, 7c and 7d may be made of any suitable material. For example, use can be made of polyurethane elastic yarn, shaped film mainly containing SEBS, and filament of foamed resin or natural rubber. Elastic spun-bonded nonwoven fabric or elastic melt-blown nonwoven fabric may also be used by slitting it into strips.

For example, the sheet 20 formed to have a wavy form is stretched by 2 times in the MD along which the waves are arranged, and the elastic members 7a, 7b, 7c and 7d are adhered to the sheet 20 in such a manner that the elastic members 7a, 7b, 7c and 7d are sandwiched between the two folded portions of the stretched sheet 20 under the condition where the elastic members 7a, 7b, 7c and 7d are stretched by 1.3 times. When the elastic contractive force where one of the elastic members is stretched by 1.3 times is 98 mN, the total elastic contractive force of the four elastic members is 392 mN. When the plural elastic members 7a, 7b, 7c and 7d are adhered to the sheet 20 and the elastic members are stretched by 1.3 times, the elastic contractive force attained by the elastic members and the sheet is preferably from 196 to 1,470 mN, and more preferably from 294 to 784 mN.

As shown in FIG. 3, the leakage preventing wall 5 has such a structure in the intermediate part of the absorbent article 1 that the wavy sheet 20 is folded into two at the free end 6, and one end 20A of the folded sheet 20 is adhered and fixed to the front surface sheet 13 at the position outside the absorbent core 12, for example, with a hot-melt adhesive. The other end 20B of the folded sheet 20 is adhered and fixed to the back surface sheet 11 directly or via a reinforcing sheet with a hot-melt adhesive at a flap part formed at each side in the width direction (X direction) of the absorbent article 1. It is also possible that one end 20A of the sheet 20 is adhered to the front surface sheet 13 alcove the absorbent core 12, and the leakage preventing wall 5 upstands above the absorbent core 12.

In FIG. 3, the leakage preventing wall 5 has a side wall part 15 upstanding on the surface 2a and a skin contacting part 16 extending from an upper end of the side wall part 15 toward the outside of the absorbent article 1 in the width direction in substantially parallel to the surface 2a. The top parts 20a and the bottom parts 20b of the sheet 20 constituting the leakage preventing wall 5 are directed to the upstanding direction in the side wall part 15 and are directed to the width direction in the skin contacting part 16.

Therefore, the leakage preventing wall 5 has a high buckling strength at the side wall part 15 against the load from the upper side, so that the leakage preventing wall 5 is not easily collapsed but can maintain the steric shape thereof. Furthermore, because the MD of the sheet 20 along which the waves are arranged is directed to the longitudinal direction (Y direction) of the leakage preventing wall 5, the leakage preventing wall 5 is easily deformed in the longitudinal direction (Y direction).

Since the skin contacting part 16 is in substantially parallel to the surface 2a, it is easily in tightly contact with the skin of the wearer, and the leakage preventing wall 5 is difficult to leave from the skin. Because the MD of the sheet 20 along which the waves are arranged is directed to the longitudinal direction (Y direction), moreover, the skin contacting part 16 is easily incurvated by following the curvature in the Y direction of the absorbent article 1, and the skin contacting part 16 is easily deformed by following the body shape of the wearer.

In the side wall part 15 of the leakage preventing wall 5, a fold inducing part 17 is provided at the middle in the height direction thereof (i.e., at the middle between the upper end and the lower end thereof). The fold inducing part 17 extends in the longitudinal direction (Y direction) of the absorbent article 1.

The elastic member 7a is provided at the fold inducing part 17, the elastic member 7b is positioned at the folded part (border) between the side wall part 15 and the skin contacting part 16, and the elastic member 7d is positioned at the free end 6 where the sheet 20 is folded into two.

As shown in FIG. 8B showing the fold inducing part 17, the wavy form is not formed in the sheet 20 in the region (ii). In the region (ii), the folded sheet 20 is compressed from both sides while sandwiching the elastic member 7a between the two folded portions thereof, so that the wavy form is collapsed. Since the sheet 20 is compressed in the region (ii), the fiber density of the sheet 20 in this region (ii) becomes higher than the fiber density in the other regions (i) where the wavy form is formed. Because the sheet 20 has a higher density in the region (ii) (i.e., because the region (ii) has no wavy form), the fold inducing part 17 is easily folded toward the outside when a pressure from the wearer's body acts on the skin contacting part 16.

As shown in FIG. 3, furthermore, at the position where the elastic member 7b is provided and at the free end 6 where the elastic member 7d is provided (i.e., at both side edges of the skin contacting part 16), the sheet 20 is also compressed while sandwiching the elastic members 7b and 7d between the two folded portions thereof to collapse the wavy form. As a result, the sheet 20 has a higher density at the positions where the elastic members 7b and 7d are provided than that at the position where the sheet 20 is imparted with the wavy form.

Therefore, the skin contacting part 16 is easily folded from the side wall part 15, and the skin contacting part 16 is easily directed to face the skin of the wearer. At the free end 6, furthermore, the sheet 20 can reliably maintain the folded shape with the elastic member 7d sandwiched therewith.

The remaining one elastic member 7c is positioned at the substantially middle part between two side edges of the skin contacting part 16. The sheet 20 is maintained to have the wavy form at the position where the elastic member 7c is provided, and only the back surfaces of the plural bottom parts 20b of the wavy form of the sheet 20 are adhered to the elastic member 7c. Therefore, the sheet 20 in the skin contacting part 16 can easily contract in the MD along which the waves are arranged owing to the elastic contractive force of the elastic member 7c.

However, it is also possible that the sheet 20 is imparted with the wavy form in the regions where the other elastic members, such as the elastic member 7d, are provided so that only the back surfaces of the bottom parts 20b of the sheet 20 are adhered to the elastic members, such as the elastic member 7d.

Moreover, it is also possible that the sheet 20 has a lower density in the region (ii) where the elastic member 7a is provided shown in FIG. 8B and in the regions where the elastic members 7b and 7d are provided, than in the other parts thereof (e.g., the region (ii) where the elastic member 7a is provided and the regions where the elastic members 7b and 7d are provided are not formed with the wavy form from the beginning). With such a structure, the side wall part 15 is easily folded at the fold inducing part 17, and the skin contacting part 16 and the side wall part 15 are easily folded at the position where the elastic member 7b is provided. Furthermore, the sheet 20 can be easily folded into two at the position where the elastic member 7d is provided.

In the leakage preventing wall 5, moreover, an inner gap is formed between the two folded portions of the sheet 20 by providing the wavy form. Owing to the presence of the inner gap, a body fluid is difficult to permeate the leakage preventing wall 5 to thereby improve the leakage preventing effect. Furthermore, the inner gap softens the contact feeling to the skin of the wearer to thereby improve the wear feeling.

FIG. 4 shows the folded state of the leakage preventing wall 5 in the front part 3 and the back part 4 of the absorbent article 1. In the front part 3 and the back part 4, the leakage preventing wall 5 in such a folded state is adhered or fused on the surface (on the surface sheet 13). In these parts, the side wall part 15 is folded into two with the fold inducing part 17 moved toward the outside in the width direction, and the skin contacting part 16 is further superposed thereon, whereby the leakage preventing wall 5 is fixed on the surface 2a in such a state that it is folded at three axes to have a four-layer structure.

Since both the ends in the longitudinal direction of the leakage preventing wall 5 are adhered in the folded state shown in FIG. 4 in the front part 3 and the back part 4, the absorbent article 1 in a free condition is incurvated in the longitudinal direction as shown in FIG. 1 due to the elastic contractive force of the elastic members 7a, 7b, 7c and 7d, and as a result, in the intermediate part 2, the fold inducing part 17 is directed to the outside in the width direction, and the leakage preventing wall 5 upstands in a Σ form.

Because the fold inducing part 17 to be directed to the outside in the width direction is provided at the middle part between the upper end and the lower end of the side wall part 15 of the leakage preventing wall 5, the side wall part 15 is folded at the fold inducing part 17 when the skin contacting part 16 is in contact with the skin of the wearer and a pressure acts on the skin contacting part 16 in the direction toward the surface 2a. Therefore, the upper end of the side wall part 15 and the skin contacting part 16 are prevented from falling down toward the center of the surface 2a of the absorbent article 1, and thus the liquid absorbent area of the surface 2a is prevented from decreasing. Therefore, the liquid absorbent ability of the absorbent article is not lowered.

In order to certainly fold the side wall part 15 at the fold inducing part 17 on application of load on the skin contacting part 16, it is preferred that the height dimension of the side wall part 15 where it upstands in the height direction to have a perpendicular plane is from 5 to 30 mm, and more preferably from 10 to 20 mm. When the dimension is smaller than the range, the side wall part 15 may be difficult to be folded into two. When the dimension exceeds the rage, the height of the leakage preventing wall 5 becomes too large, and the steric shape of the leakage preventing wall 5 is difficult to be maintained.

The width dimension of the skin contacting part 16 is preferably from 5 to 25 mm, and more preferably from 10 to 15 mm. When it is smaller than the range, the contact to the skin becomes poor. When it is larger than the range, there is a possibility that the skin contacting part 16 gives uncomfortable feeling to the wearer when it is in contact with the skin of the wearer.

In order that the leakage preventing wall 5 can be easily folded to the steric shape shown in FIG. 3 or the folded state shown in FIG. 4, it is preferred that the wavy form is not formed in the sheet 20 constituting the leakage preventing wall 5 only at the free end 6 and the fold inducing part 17 of the leakage preventing wall 5, or in alternative, a difference in density is provided between the fold inducing part 17 and the other parts.

In the leakage preventing wall 5 upstanding to form the steric shape shown in FIG. 3, the region 15a under the fold inducing part 17 is slanted to leave from the surface 2a toward the outside in the width direction. In the case where a body fluid is attached to the slanted region 15a, the body fluid tends to flow down the slanted region 15a toward the front surface sheet 13 along the bottom parts 20b. Therefore, the body fluid is difficult to remain attached to the leakage preventing wall 5, and leakage in the width direction can be prevented.

Figure 6:
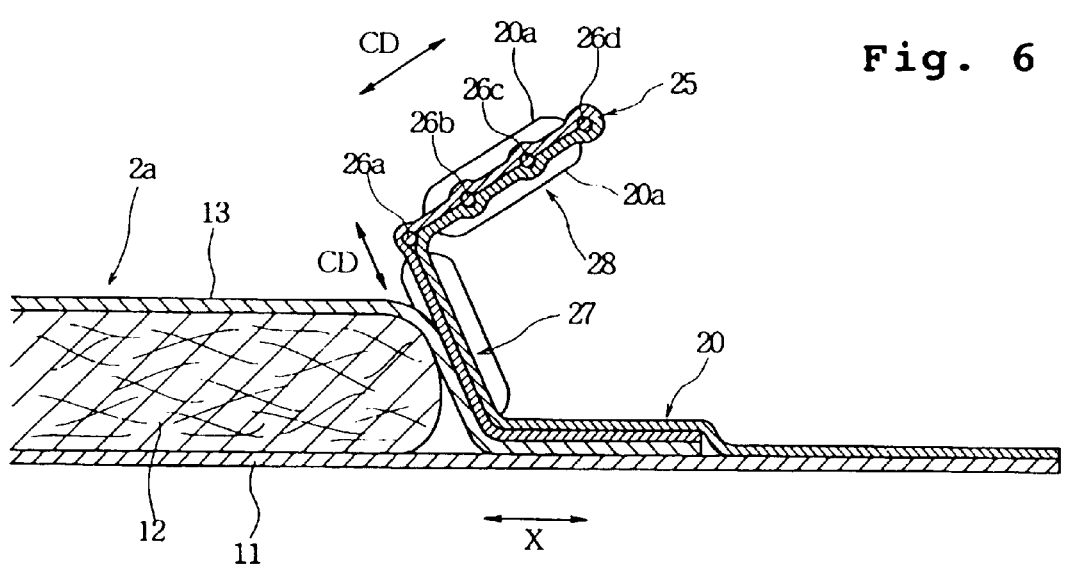
FIG. 6 is an enlarged cross sectional view of a second embodiment corresponding to FIG. 3.

FIG. 6 shows a second embodiment of the invention and shows an upstanding steric shape of a leakage preventing wall 25 in the intermediate part 2 of the absorbent article 1 as similar to FIG. 3.

The leakage preventing wall 25, as similar to the foregoing embodiment, is formed such that the sheet 20 having a wavy form is folded into two while sandwiching four elastic members 26a, 26b, 26c and 26d between the two folded portions thereof. The individual elastic members are adhered to the bottom parts 20b of the respective folded portions of the sheet 20.

In the leakage preventing wall 25, a side wall part 27 upstands on a slant from a position outside the region where the absorbent core 12 is provided, and a skin contacting part 28 upstands on a slant from the upper end of the side wall part 27 to leave from the surface 2a toward the outside in the width direction. Therefore, a body fluid given to the skin contacting part 28 falls down the surface of the sheet 20 of the wavy form toward the surface 2a, and is given to the absorbent core 12 to be absorbed by the absorbent core 12.

In the embodiment shown in FIG. 6, also, the density of the sheet 20 is made higher by collapsing the wavy form of the sheet 20 in the positions where the elastic members 26a and 26d are provided, than in the other parts, or in alternative, the density of the sheet 20 is made lower in the positions where the elastic members 26a and 26d are provided than in the other parts.

Therefore, the side wall part 27 and the skin contacting part 28 can be easily folded at the position where the elastic member 26a is provided, and the sheet 20 can reliably maintain the folded shape at the free end where the elastic member 26d is provided.

In the positions where the other elastic members 26b and 26c are provided, the sheet 20 has the wavy form, and the elastic members 26b and 26c are adhered only to the back surface of the bottom parts 20b of the wavy form of the sheet. Therefore, the sheet in the skin contacting part 28 can be easily contracted by the elastic members 26b and 26c.

As described in the foregoing, because the leakage preventing wall 5 or 25 is formed by using the sheet 20 formed to have the wavy form, a body fluid is liable to flow toward the absorbent core along the bottom parts 20b of the wavy form of the leakage preventing wall. Because the sheet 20 forming the leakage preventing wall 5 or 25 is formed to have the wavy form and has a lower density in the midway part 20c, the body fluid can be absorbed at the midway part 20c, and furthermore, because a gap is formed between the two folded portions of the sheet 20 owing to the wavy form, the body fluid can be blocked with the leakage preventing wall effectively, so that the leakage of the body fluid out of the leakage preventing wall hardly occurs.

In the leakage preventing wall 5 or 25, moreover, because the direction of upstanding the side wall part 15 or 27 from the surface 2a agrees with the CD along which the top part and the bottom part of the wavy form extend, the leakage preventing wall can reliably maintain the steric shape thereof. Furthermore, because the skin contacting part 16 or 28 has the wavy surface, the contact feeling to the skin is softened to improve the wear feeling.

As has been described above, advantages of the absorbent article of the invention may include one or more of the following:

The leakage preventing wall is difficult to fall down on the front surface side to prevent the reduction of the liquid absorbing ability upon wearing;

The leakage preventing wall is difficult to be contaminated with a body fluid, and a body fluid attached to the leakage preventing wall can be easily led to the absorbent surface; and Because the CD of the sheet forming the leakage preventing wall, along which the top parts and the bottom parts of the wavy form of the sheet extend, is directed to the upstanding direction from the surface in the side wall part and to the skin contacting part, the leakage preventing wall can reliably maintain the steric shape thereof, and the contact feeling to the skin is softened.

Here, "comprises/comprising" when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a body portion including a liquid permeable front surface sheet for facing the wearer, a back surface sheet, and an absorbent layer sandwiched between the front surface sheet and the back surface sheet; and
   leakage preventing walls extending in a longitudinal direction of the body portion and arranged at two sides thereof lying opposite one another in a crossward direction perpendicular to the longitudinal direction,
   the leakage preventing wall including a side wall part having a lower end thereof fixed on the surface of the body portion and rising from the surface of the body portion and a skin contacting part bent from an upper end of the side wall part outwardly of the body portion in the crossward direction substantially parallel to the surface of the body portion,
   the side wall part being folded at a fold inducing part to have a lower part outwardly slanted to extend from the lower end of the side wall part to the fold inducing part and an upper part inwardly slanted to extend from the fold inducing part to the upper end of the side wall part, the fold inducing part being positioned at a middle between the upper and lower ends of the side wall part to extend in the longitudinal direction of the body portion, wherein both ends in the longitudinal direction of the leakage preventing wall are fixed on the surface of the body portion in such a state that the upper part of the side wall part is superposed on the lower part of the side wall part and the skin contacting part is superposed on the upper part of the side wall part.

2. The absorbent article as set forth in claim 1, wherein elastic members for exhibiting a contractive force in the longitudinal direction are attached to the fold inducing part and the skin contacting part.

3. The absorbent article as set forth in claim 1, wherein the leakage preventing wall comprises a corrugated nonwoven fabric having hills and valleys which alternate with each other in the longitudinal direction and individually extend perpendicular to the longitudinal direction.

4. The absorbent article as set forth in claim 3, wherein the fold inducing part has a density that is different from a density of other parts of the side wall part.

5. The absorbent article as set forth in claim 4, wherein at least one of side edges of the skin contacting part has a density that is different from a density of other parts of the leakage preventing wall.

6. The absorbent article as set forth in claim 3, wherein the corrugation of the nonwoven fabric is interrupted in the fold inducing part.

7. The absorbent article as set forth in claim 6, wherein the corrugation of the nonwoven fabric is interrupted in at least one of side edges of the skin contacting part lying opposite one another in the crossward direction.

\* \* \* \* \*